United States Patent
Levin

(12) 
(10) Patent No.: US 6,316,750 B1
(45) Date of Patent: Nov. 13, 2001

(54) APPARATUS FOR WARMING MEDICAL PADS

(76) Inventor: Andrew Levin, 4450 NE. Indian River Dr., Jensen Beach, FL (US) 34957

( * ) Notice: Subject to any disclaimer, the term of this patent is extended or adjusted under 35 U.S.C. 154(b) by 0 days.

(21) Appl. No.: 09/547,006

(22) Filed: Apr. 11, 2000

Related U.S. Application Data

(60) Provisional application No. 60/128,733, filed on Apr. 12, 1999.

(51) Int. Cl.[7] ............................... F27D 11/00; A61F 7/08
(52) U.S. Cl. .......................... 219/438; 219/386; 219/433; 219/428; 222/146.5; 604/291
(58) Field of Search .................................... 219/385, 386, 219/399, 480, 432, 435, 438, 394, 428; 604/291; 272/146.5

(56) References Cited

U.S. PATENT DOCUMENTS

| | | | | |
|---|---|---|---|---|
| D. 362,493 | * | 9/1995 | Begum | D23/314 |
| D. 390,645 | * | 2/1998 | Hanrahan et al. | D23/332 |
| 1,659,719 | * | 2/1928 | Blake | 219/385 |
| 2,576,874 | * | 11/1951 | Acton | 219/385 |
| 2,577,870 | * | 12/1951 | Aston | 219/387 |
| 3,051,582 | * | 8/1962 | Muckler et al. | 219/386 |
| 4,163,896 | * | 8/1979 | McAvinn et al. | 219/386 |
| 4,215,267 | * | 7/1980 | Kaebitzsch | 219/432 |
| 4,419,568 | * | 12/1983 | Overloop | 219/439 |
| 4,495,402 | * | 1/1985 | Burdick et al. | 219/214 |
| 4,810,859 | * | 3/1989 | Anabtawi et al. | 219/535 |
| 4,857,708 | * | 8/1989 | DeMars | 219/385 |
| 4,967,061 | * | 10/1990 | Weber, Jr. et al. | 219/438 |
| 5,208,896 | * | 5/1993 | Katayev | 219/432 |
| 5,210,396 | * | 5/1993 | Sanders | 219/386 |
| 5,408,576 | * | 4/1995 | Bishop | 219/386 |
| 5,977,520 | * | 11/1999 | Madson, Jr. et al. | 219/430 |

* cited by examiner

Primary Examiner—Joseph Pelham
(74) Attorney, Agent, or Firm—Kevin Redmond

(57) ABSTRACT

An insulated case designed to keep medical pads warm and in a condition ready for application over a period of hours. The case typically includes a cover, multiple internal containers and a source of controlled heat to warm the pads. The pads, after being saturated with a medication such as alcohol, are stored in the internal containers where they are raised in temperature by the controlled heat source to a predetermined temperature range and maintain within that temperature range. At the same time, the vapor pressure is maintained at a level within the internal containers to prevent the escape of the alcohol from the pads through evaporation. The safety features of this apparatus include an over temperature alarm and automatic shut off as well as an over pressure alarm and vent, all of which operate even when there is a power failure. Internal containers are individually insulated and are removable for transport to wherever they are needed. Each internal container includes a temperature sensing device which indicates whether the pads are still within the desired temperature range after they have been removed from the source of controlled heat.

10 Claims, 3 Drawing Sheets

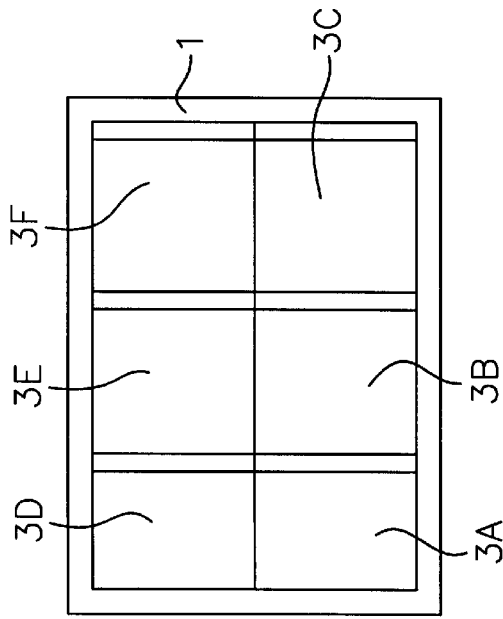
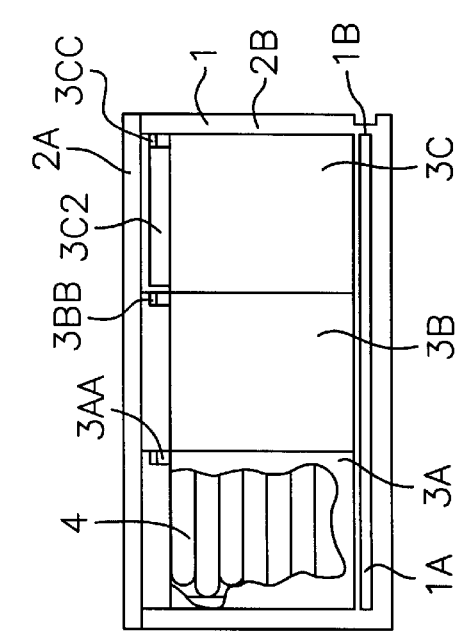
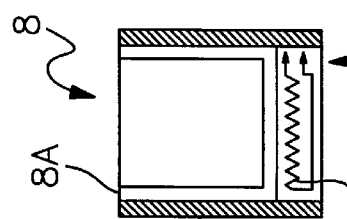
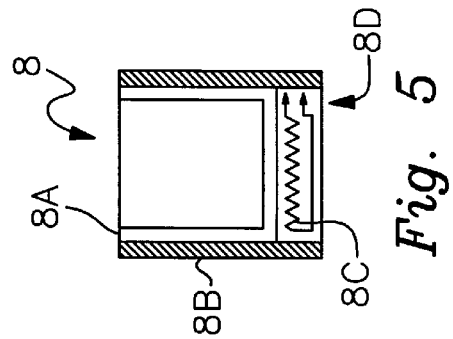
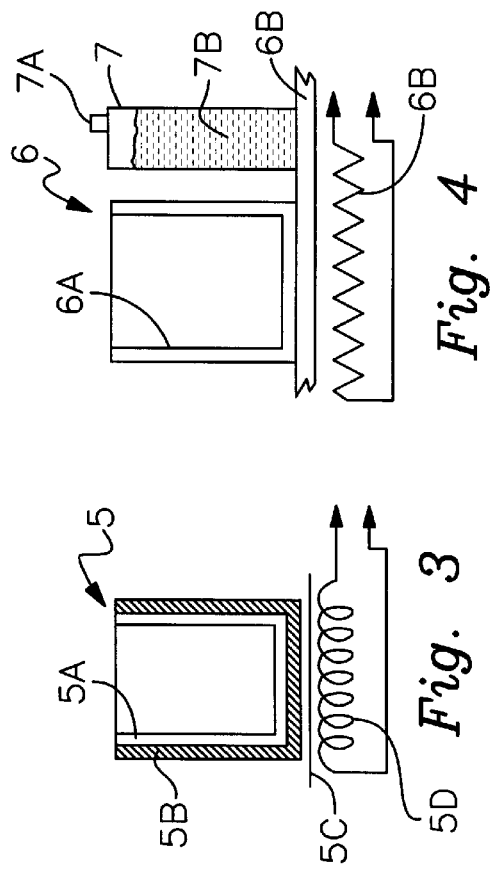

APPARATUS FOR WARMING MEDICAL PADS

This application claims benefit to Provisional Application No. 60/128,733 filed Apr. 12, 1999.

BACKGROUND

1. Field

The present invention relates to maintaining medical pads within a predetermined temperature range and more particularly to preserving such pads in a ready to use condition over a period of hours.

2. Prior Art

Prior to an injection or taking a blood sample, the skin is usually sterilized by means of alcohol applied with a medical pad. Normally, the alcohol and the pad are stored at room temperature. As soon as the alcohol is applied to the pad, it begins to evaporate and cool the pad. The pad becomes cool to the touch and its initial application cools the area to which it is applied. This initial cooling is added to by the continued evaporation of the alcohol on the skin. The application of the pad is uncomfortable for the patient and it tends to make the veins withdraw from the skin, making the drawing of a blood sample difficult.

There are medical pad warming devices currently in existence as evidenced by prior art U.S. Pat. No. 3,867,939 by Moore, U.S. Pat. No. 3,976,049 by Yamashita and U.S. Pat. No. 4,107,509 by Scher. Moore describes a disposable sterile temperature controlled applicator intended to control the temperature of a particular part of the body, rather than the temperature of a medical applicator pad. Yamashita describes a chemically produced warmer which is generally not reuseable and therefore inappropriate for the present application. Scher describes a pad intended to apply heat to the body rather than a pad intended to sterilizer an area of the skin.

SUMMARY

It is an object of the present invention to provide a medical pad warming device that is reuseable and can operate continuously for a period of hours without the need to add chemicals.

It is an object of the present invention to provide a medical pad warming device that maintains the pads within a prescribed temperature range.

It is an object of the present invention to provide a medical pad warming device that prevents the evaporation of the medication applied to the pads while the pad is maintained at a temperature which makes the pad ready for immediate application.

It is an object of the present invention to provide a medical pad warming device that includes a means for the convenient transport of medical pads to a location that is remote from power and heat.

It is an object of the present invention to provide a medical pad warming device that includes a means for continually monitoring the temperature of the pads at a location that is remote from a source of power or heat.

It is an object of the present invention to provide a medical pad warming device that is safe for use in the operating room as well as other areas of medical facilities.

The present invention includes an insulated case carrying multiple internal containers and a source of controlled heat to warm medical pads, such as alcohol pads, and hold them in a ready condition for immediate use over long periods of time. The pads, after being saturated with alcohol, are stored in the internal containers where they are raised in temperature by the controlled heat source to a predetermined temperature range and maintained within that predetermined temperature range. The insulated case is covered so that vapor pressure can be maintained at a level within the internal containers that prevent the escape of the alcohol from the pads through evaporation.

The safety features of this apparatus include a power failure alarm, an over temperature, over pressure and over voltage alarm, an over pressure vent and an automatic shut off alarm, all of which continue to operate even when there is a power failure. One embodiment of the present invention provides for heating without the use of electricity for situations where electrical power is not available. Internal containers are individually insulated and are removable for transport to wherever they are needed. They are also individually covers to prevent evaporation. Each internal container includes a temperature sensing device which indicates whether the pads are still within the desired temperature range after they have been removed from the source of controlled heat. To save time in emergency situations, individual containers include a flag or a window which indicated when the pads within a container are used up.

BRIEF DESCRIPTION OF THE DRAWINGS

FIG. 1 is a side cross sectional view of the present invention showing the external insulated case and the individual internal containers.

FIG. 2 is a top view of the present invention with the cover removed from the main case to show the internal containers.

FIG. 3 is a side cross sectional view of an insulated internal container which includes an an induction heating system.

FIG. 4 is a side cross sectional view of a metal internal container which can be heated by either a resistance heating element or a hot fluid source.

FIG. 5 is a side cross sectional view of an insulated internal container which includes an individual internal heating element.

DETAILED DESCRIPTION OF THE INVENTION

A first embodiment of the present invention is shown in FIG. 1. This embodiment comprises an external case 1, an internal heating element 1A, a power connection cavity 1B, a cover 2A, an insulated wall 2B, first, second and third internal containers 3A, 3B and 3C respectively, and first, second and third grips 3AA, 3BB, 3CC on containers 3A, 3B and 3C respectively. The first internal container 3A is shown broken away to reveal a plurality of medical applicator pads that are stacked within this container. The grips are designed to facilitate gripping and lifting the containers out of the case. The grips can vary is shape and size from a simple groove such as is shown in the side of the container in FIG. 1 to small individual handle on each container.

In the use of the first embodiment shown in FIG. 1, medical applicator pads soaked in a medication, such as alcohol, are stacked in each of the three containers in the manner shown. A power line is connected to the internal heating element 1A at the power connection cavity to warm the medical pads stacked within these containers. The pads remain in their containers until they reach a desired temperature such as 100 degrees F. This temperature is checked in this first embodiment by placing among the pads a temperature measuring device, such as a thermometer. Once the desired temperature has been reached, the power is removed by disconnecting the power manually. The power is reapplied when the temperature drops to a level such as 90 degrees F.

A cover 2A located on top of the case seals the case to prevent the alcohol from evaporating. Each of the internal containers also includes its own cover such as container cover 3C2 on container 3C to seal the individual internal containers so that they can be removed from the case and brought to where they are needed. This arrangement reduced the number of pad warming apparatus required in an area. The pads tend to stay warm and medicated does not evaporate because the pads are in an insulated and sealed container.

To facilitate the use of the pads in several different locations such as different stations in an operating room, a container is lifted out of the case 1 by means of the grip and brought to a desired location. All the internal containers are similarly removable to service a plurality of stations simultaneously with only one central heating unit. A number of case sizes are available to handle various size facilities. For example, the case shown in plan view in FIG. 2 holds six internal containers including containers 3D, 3E, and 3F in addition to containers 3A, 3B and 3C.

Figure 6:
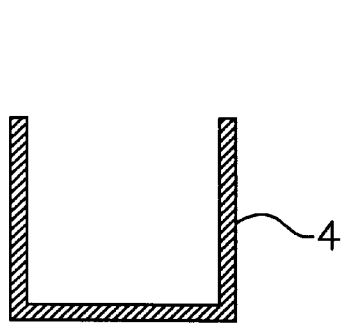
FIG. 6 shows a cross sectional view of an insulating cover which can accept a metal internal container to provide insulation for the internal container when it is transported away from the case and its associated heat source.

To retain the heat, the walls of the case and the walls of the internal containers include insulation, although the individual containers have in the walls of this first embodiment relatively little insulation as compared to the case walls to aid in the transfer of heat through the container to the pads. In a second embodiment of the invention, the container walls are made of a conductive material, such as stainless steel, to increase the heat transfer through the container walls. To retain the heat within the stainless steel containers once they are removed from the case, they are inserted in an insulated carrier such as the insulated carrier 4 shown in the cross sectional view of FIG. 6.

A third embodiment of the invention is shown in FIG. 3. In this embodiment, a container 5 includes an outer wall of insulating material 5B which covers a metal inner wall 5A. The container is supported on an insulating surface 5C. Beneath the surface 5C is an induction coil 5B which, when activated by alternating current, induces a current within the bottom of the metal inner wall 5A causing it to become heated. Radio Frequency (RF) alternating current is usually used in induction heading systems. A shielded RF generator is included before the induction coil. The shielding prevents radiation of the RF into the operating area. This feature eliminates the need to place the containers in an insulating carrier such as carrier 4. The outer insulating wall 5B is bonded to the inner wall and remains with the inner wall to keep the pads warm when the container is removed from its position over the induction coil and brought to a work station where the pads are to be disbursed. The insulating walls not only maintain the temperature of the pads, but also facilitate the transport of the the container because the insulation isolates the hot inner wall from the hand of the person carrying the container.

In a forth embodiment, metal containers are adapted to gain the benefits of insulated containers in heat retention and transport by applying an outside insulating wall to only the sides of the container where they will be held, while leaving the bottom surface uninsulated to allow the transfer of heat to the container by conductive means, such as by transferring the heat by conduction from a heating element such as 1A, shown in FIG. 1. This embodiment is identical to that shown in FIG. 3, only the insulation layer 5B is removed from the bottom of the container. To reduce heat loss through the bottom of the container at a work station away from the beat source, the container is placed on an insulating surface which can vary from a special insulated pad design for this purpose down to something as simple as a folded paper towel.

FIG. 4 shows a fifth embodiment of the invention designed for use in cases where electrical power is lost or when electrical power cannot be used for heating the pads. This embodiment includes a container 6 having a conductive container wall 6A, a conductive support platform 6B and a flask 7. The flask is designed to hold hot water 7B which is fed into the flask through inlet spout 7A. This embodiment also includes a back up heating element 6C which is placed below the conductive platform 6B. Both the flask and the container rest on and are thermally connected to the platform 6B to enable heat from the flask to be transferred to the container by way of the platform and heat from the heating coil to be transferred from the coil to both the container and the water in the flask.

In the operation of the embodiment shown in FIG. 4, the pads are stored in the container 6 while hot water is fed through the spout 7A into the flask 7. The heat from the hot water is transferred through platform 6B to the container 6 and the medical pads stored in this flask. Hot water, which is available in every major medical facilities and even in the field, can be used to heat the pads where there is no electrical power or where the use of electrical power may cause problems This embodiment may be used in another way. The electrical heating coil 6C makes it possible to use this unit in a conventional way where the heating coil heats the pads by way of the conductive platform 6B. It is also possible to use this coil to heat the water in the flask and then remove the entire unit to a remote location where electrical power is not available or inconvenient to reach. The heated water will enable this unit to keep the pads heated for a long period of time without the use of electrical power. The hot water serves as a heat reservoir. Although not show, the features contained in other embodiments such an insulated case, a sealed lit and multiple removable containers may be employed as well.

FIG. 5 shows a sixth embodiment of the invention which includes a built in heating coil for a single container. This Figure includes a container 8 having an inner metal walls 8A and outer insulating walls 8B. Built into this unit below the base of the container is a heating coil 8C with a power receptacle 8D for applying power to the coil 8C. Power applied to the coil heats the container as there is a conductive connection between the coil and the base of the cup without any insulation between the two. This embodiment is simple to use and low in cost. The pads are stacked in the container and power is applied to the heating coil to heat the pads. Heat is retained when power is shut off. The unit can be disconnected from the power line at the receptacle and moved to where the pads are needed. The pads are kept warm by insulation which is contained in the walls and also about the base of the unit.

Figure 7:
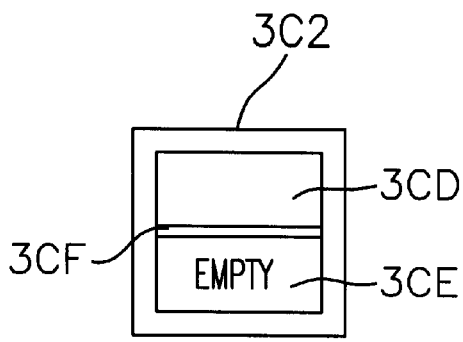
FIG. 7 is a bottom view of an insulating cover which includes a window into which a flag carrying the word "EMPTY" is moved when the container no longer contains pads.

FIG. 7 is the bottom view of an embodiment in which the cover 3C2 for internal container 3C includes a window 3CD and an "EMPTY" sign that can be moved into the window area manually with the aid of grip 3CF. The sign shows when a container is empty without the need to open the cover. This is advantageous in busy operating rooms to prevent empty containers from being taken to operating stations for use only to later find that the containers are empty when they are opened to obtain a pad. The word "EMPTY" is placed on both sides of the sign so that it can be read when the cover is opened or closed. A simpler equivalent is to have the window on the cover or on the side of the case so that the quantity of pads remaining can be quickly ascertained by viewing the contents of the container through the window.

Figure 8A:
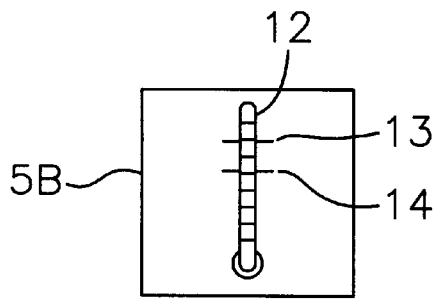
FIG. 8A is a side view of an internal container carrying a temperature indicating device.
Figure 8B:
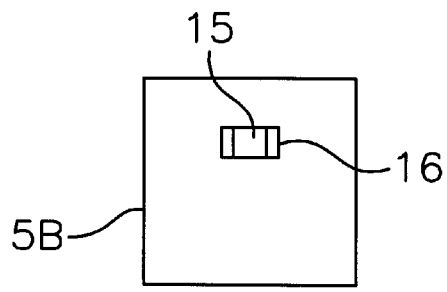
FIG. 8B is a side view of an internal container with a temperature indicating device and a means for showing and magnifying temperatures in the range of interest.

FIGS. 8A and 8B show embodiments of the present invention which carry direct reading temperature indicating devices on the internal containers to show when the internal containers need to be reheated to keep the pads within the desired temperature range. FIG. 8A shows a container with a conventional thermometer built into the side wall of the container behind a clear insulating layer which enables the user to read the temperature by simply looking at the side of the container carrying the thermometer. FIG. 8B is an improvement over the simple system of FIG. 8B in that the thermometer or other temperature indicating device is exposed for viewing only over the desired temperature range. This temperature range is viewed through a small built in magnifying glass so that the desired temperature range can easily be seen.

An equivalent of the above described temperature indicating devices is a bimetal temperature sensors which produce an electrical current that is read on a small meter or which activates a flag when the temperature is within the desired range. Current necessary for logic circuitry is generated by low cost solar cells similar to those used on low cost calculators. The solar cells are activated by the natural or artificial light present in operating rooms or other medical facilities where the present invention is employed.

Figure 9:
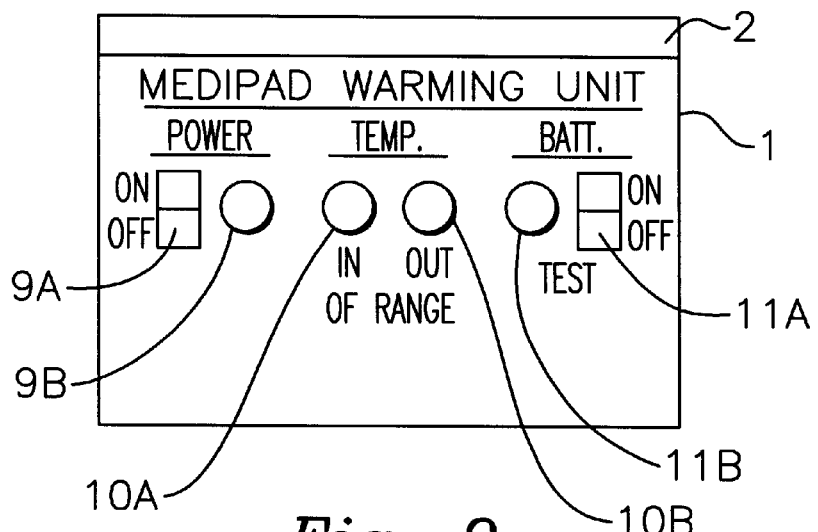
FIG. 9 shows a seventh embodiment of the invention, dipicting power switches and indicator lights.

FIG. 9 shows a seventh embodiment of the present invention which includes a case 1 and a cover 2 as well as internal containers similar to the embodiments shown in FIGS. 1 and 2; however, this embodiment also includes on one side of its case a power on off switch 9A, a power on light 9B, a pair of temperature indicating lights 10A and 10B, a battery test light 11B, and a battery test switch 11A. This unit is powered by a standard 120 volt or 220 volt line which can be applied to the system by the on off switch 9A. If the power line is activated, this will be indicated by the light 9B which will be lit. The two temperature indicating lights 10A and 10B indicate whether the internal containers are in or out of the desired temperature range. An internal alarm is activated when there is a power failure or the temperature of the pads is out of the desired range. The alarm can be temporarily deactivated. The battery activates the alarm and the temperature indicating lights when there is a power failure so that that if the pads are still sufficiently warm to use, the operator will know that and can continue to use the pads despite the power outage. The battery test switch is a momentary on switch which turns on light 11B during the activation of this switch to indication the condition of the battery.

Figure 10:
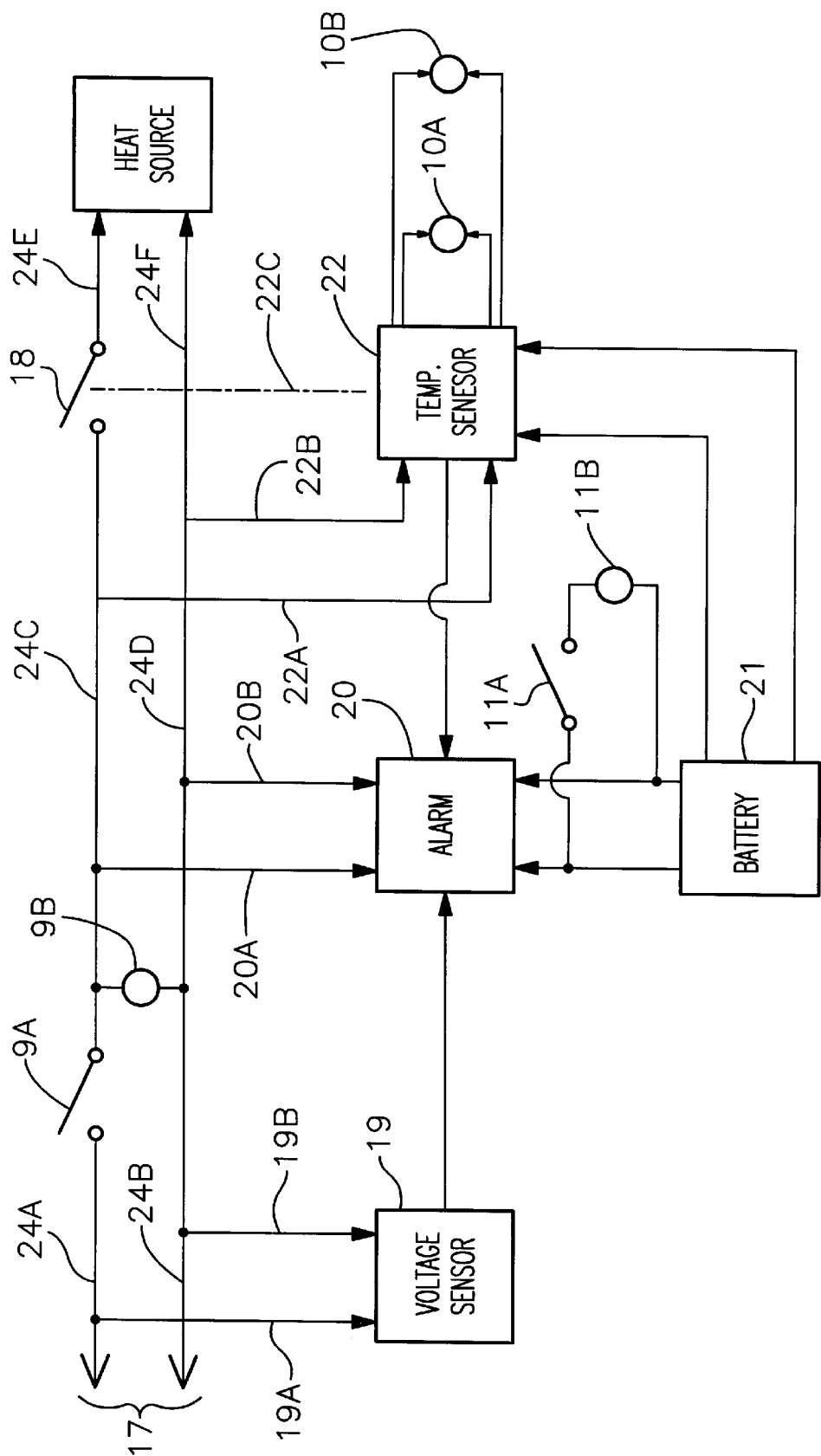
FIG. 10 is an electrical block diagram of the present invention showing the connections to the alarm system and the connection to the back up battery.

FIG. 10 is a block diagram showing the interconnection of the most important components of the embodiment shown in FIG. 9. This Figure includes the five major components of this system which are a voltage sensor 19, an alarm 20, a battery 21, a temperature sensor 22 and heat source 23. This Figure also includes switches 9A, 11A, and 18, as well as lights 9B, 10A, 10B and 11B. Switch 18 is a thermostatic switch feeding power to the heat source which is activated by the temperature sensor to maintain the pads within the desired temperature range. The temperature sensor is connected to lights 10A and 10B as well as the alarm and activates these lights and/or the alarm appropriately depending on the temperature of the pads. The battery activates the temperature sensor and these lights when there is no 120 volt power present. When the 120 volt power is off and/or the pads are out of their desired temperature range, the battery activates the alarm. The interconnection lines between the function boxes in this block diagram show the various connections necessary to accomplish these functions.

Having described my invention, I claim:

1. A medical application holding system comprising:
   (a) a case having at least side walls and a bottom forming an enclosure
   (b) means for heating the medical application pads within the case,
   (c) means for controlling the temperature and holding it within a predetermined range within said case,
   (d) a removable lid to completely close said case and to retain heat within said case while providing access to the medial application pads contained within said case, said wall being thermally insulated to retain heat within said enclosure, said means for heating a heating element, said heating element is electrical and includes means for receiving electrical power and wherein said means for controlling the temperature range within said case includes a thermostat connected to sense the temperature within the case and to modify the electrical power supplied to the electrical heating element to maintain said predetermined range of temperature within said case, and
   (e) a plurality of individual removable compartments contains within said enclosure each said compartments being capable of holding medical application pads.

2. A holding system as claimed in claim 1, wherein each of said compartments has side walls and a bottom.

3. A holder as claimed in claim 2 wherein each of said compartments include means for gripping and removing each compartment from said case, said means for gripping including for each compartment a separate projection spaced away from the projections of other compartments to provide for easy grasping and removal of a compartment from said case.

4. A holding system as claimed in claim 2, wherein each of said compartments and the case all have their own removable lids each to close their respective compartment and case to prevent the evaporation of any medication contained on the application pads, and to reduce the loss of heat from said pads.

5. A holding system as claimed in claim 4 wherein said lids and side wall of said case and said compartments are thermally insulated to further reduce the loss of heat from the pads contained within the case and compartments.

6. A holder as claimed in claim 4 wherein said bottom of said compartments and said case are thermally insulated.

7. A holding system as claimed in claim 4 wherein said compartments sidewalls and bottom are formed of thermally conductive material to aid in conducting heat contained within the case through the conductive walls of the compartments to the pads within the compartments, said system further comprising insulating containers in which to place said compartments when said compartments are removed from said case to reduce the loss of heat from said compartments.

8. A holding system as claimed in claim 4 further including sign means for indicating the absence of medical pads within the case and the compartments, said sign means including a sign marked empty detachably attachable to each of said lids, said sign being capable of being placed manually on said lids in a position to be read from outside the case and compartments when there are no pads within the case and compartments.

9. A holding system as claimed in claim 4 further comprising a direct reading temperature indicator means, said means being attached to the case in a position to be directly read from outside the case, said direct reading temperature means being thermally connected to the inside of said case to enable said indicator means to detect the temperature within said case.

10. A holding system as claimed in claim 1 further comprising:

(a) a power line for supplying power from an electrical power source to said system, (b) a first switch referred to as the power switch which has an on and off position for switching on and off said power from said power line to said system, said power switch being connected in series between said power line and said system, (c) a first indicating light, referred to as the power indicator light, connected to said power switch to receive power from said power switch and be turned on only when said power switch is in it's on position, (d) a second switch referred to as the heating element control switch, which has an on and an off position and is connected in series between said power switch and said heating element, to supply and interrupt the supply of power from said power switch to said heating element, (e) a voltage sensor means for detecting the absence of voltage on said power line and for providing an output signal when said absence of voltage occurs, said voltage sensor means being connected to said power line to detect the voltage present on said power line, (f) a temperature sensing means for detecting the temperature within said case, said temperature sensing means being connected to said heating element control switch to place said switch in it's on and off positions as necessary to maintain the temperature within the case within said predetermined temperature range, (g) a second indicator light, referred to as the out of temperature range indicator light, said out of temperature indicating light being connected to the temperature sensing means and being turned on by said temperature sensing means when the temperature within said case is out of said predetermined temperature range, (h) a third indicating light, referred to as the within range indicator light, said within range indicator light being connected to the temperature sensing means and is turned on by said temperature sensing means when the temperature within said case is within said predetermined temperature range, (i) an alarm circuit means for producing an alarm when there is no voltage on the power line, and when the temperature within said case is outside said predetermined temperature range, said alarm circuit means accepting an input from said voltage sensor means when the voltage on the power line is absent and from said temperature sensing means when the temperature in the case is out of said predetermined temperature range, said alarm circuit producing an alarm upon the receipt of said signals from said voltage sensor means and from said temperature sensing means, and (j) battery supply means for supplying power to said alarm circuit automatically when power on said power line is interrupted, said battery supply means including a battery to supply and activate the alarm circuit and temperature sensing means to provide an alarm when the temperature within the case is beyond said predetermined range when there is an absence of power on the power line.

* * * * *